(12) United States Patent
Parthasaradhi Reddy et al.

(10) Patent No.: US 7,772,399 B2
(45) Date of Patent: Aug. 10, 2010

(54) PROCESS FOR AMORPHOUS FORM OF DONEPEZIL HYDROCHLORIDE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Attunuri Narasa Reddy, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 1275 days.

(21) Appl. No.: 10/509,952

(22) PCT Filed: Apr. 2, 2003

(86) PCT No.: PCT/IN03/00136
§ 371 (c)(1),
(2), (4) Date: Oct. 4, 2004

(87) PCT Pub. No.: WO2004/087660
PCT Pub. Date: Oct. 14, 2004

(65) Prior Publication Data
US 2005/0222208 A1    Oct. 6, 2005

(51) Int. Cl.
*C07D 211/32*    (2006.01)
(52) U.S. Cl. .................. 546/205; 546/206
(58) Field of Classification Search ............ 546/205, 546/206
See application file for complete search history.

(56) References Cited

U.S. PATENT DOCUMENTS

| | | | | |
|---|---|---|---|---|
| 4,895,841 A | * | 1/1990 | Sugimoto et al. | 514/212.01 |
| 5,985,864 A | * | 11/1999 | Imai et al. | 514/321 |
| 6,649,765 B1 | * | 11/2003 | Vidyadhar et al. | 546/185 |
| 7,186,842 B2 | * | 3/2007 | Aher et al. | 546/206 |
| 2004/0102523 A1 | | 5/2004 | Broquaire et al. | |

OTHER PUBLICATIONS

Lieberman et al. "Pharmaceutical dosage forms" Marcel Dekker, p. 462-465 (1989).*
Brittain "Polymorphism in pharmaceutical solids" Marcel Dekker, p. 208-218 (1999).*
Amorphous definition CRD handbook Internet print out (2008).*
Hackh's dhemical dictionary, p. 172, "concentra(te)" (1983).*
Borchardt et al. "pharmaceutical profiling . . . " p. 101 (2004).*
O'Hara et al."Respirable . . . " Pharm. Res. v. 17, p. 955-961 (2000).*
Merck Index, p. 5818, 5936 (1976).*
Aricept "drug description" p. 1, (2010).*
"Solvent" Wikipedia, p. 1 (2010).*
Banga S, Chawla G, Bansal AK. New trends in crystallization of active pharmaceutical ingredients. Business Briefing: Pharmagenerics 2004, (Nov. 1-5).

* cited by examiner

*Primary Examiner*—Celia Chang
(74) *Attorney, Agent, or Firm*—Caesar, Rivise, Bernstein, Cohen & Pokotilow, Ltd.

(57) ABSTRACT

The present invention provides a novel process for the preparation of amorphous form of donepezil hydrochloride.

7 Claims, 1 Drawing Sheet

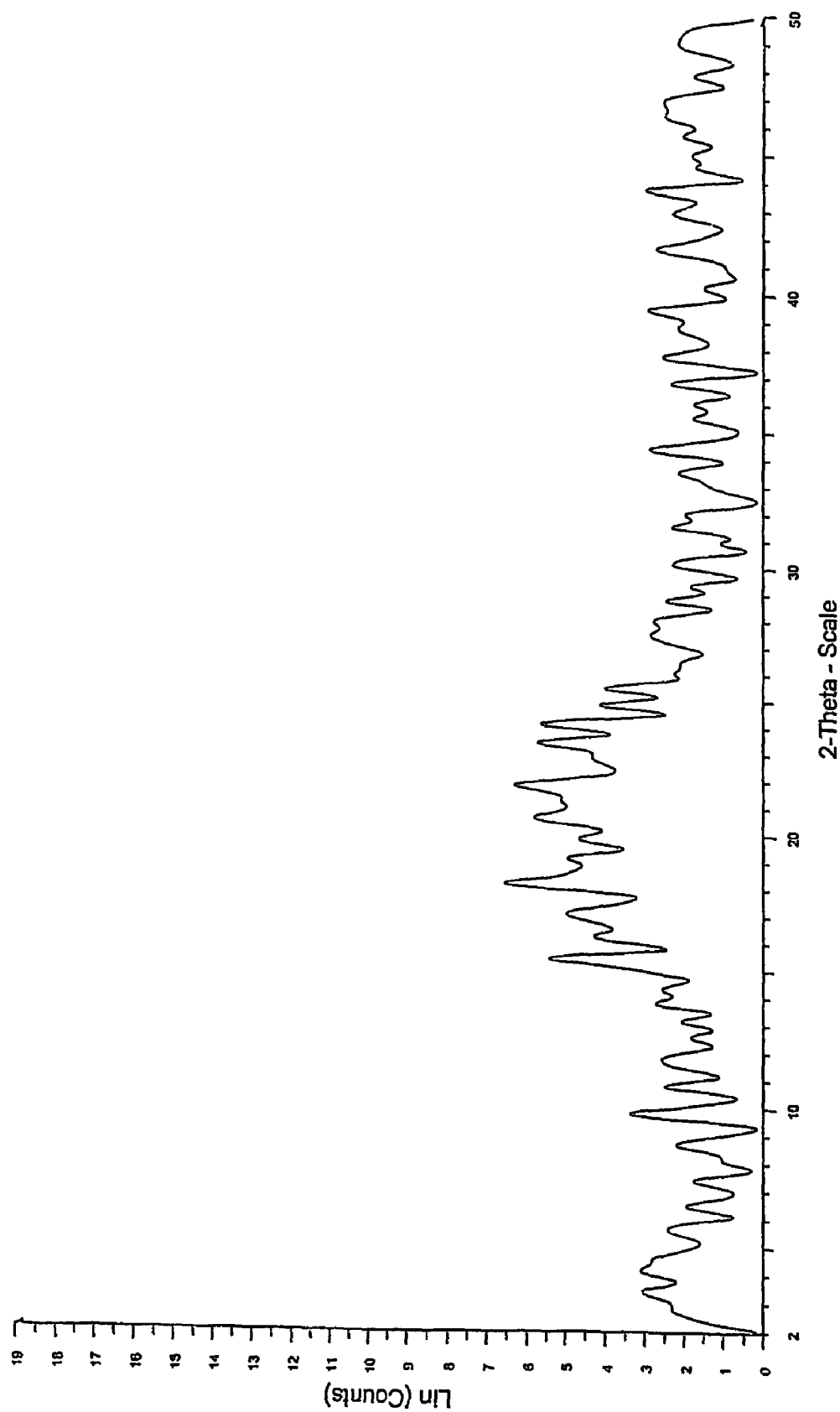

PROCESS FOR AMORPHOUS FORM OF DONEPEZIL HYDROCHLORIDE

FIELD OF THE INVENTION

The present invention provides a novel process for the preparation of amorphous form of donepezil hydrochloride.

BACKGROUND OF THE INVENTION

Donepezil hydrochloride of formula (1):

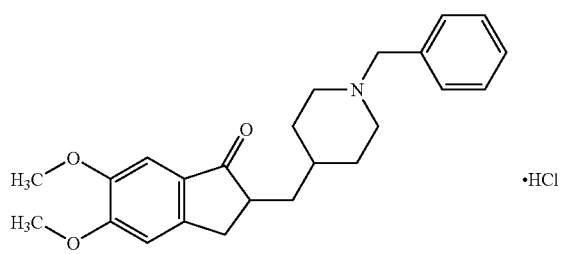

or 2,3-Dihydro-5,6-dimethoxy-2-[[1-(phenylmethyl)-4-piperidinyl]methyl]-1H-inden-1-one hydrochloride is useful for prevention and treatment of alzheimer disease. The therapeutic uses of donepezil hydrochloride and related compounds are disclosed in EP 296560. Amorphous form of donepezil hydrochloride is mentioned in U.S. Pat. No. 6,140,321.

We have discovered a simple novel process for the preparation of amorphous form of donepezil hydrochloride.

The object of the present invention is to provide a novel process for the preparation of the amorphous form of donepezil hydrochloride.

DETAILED DESCRIPTION OF THE INVENTION

The amorphous donepezil hydrochloride is characterized by having broad x-ray diffraction spectrum as in FIG. 1.

One aspect of the present invention provides a process for the preparation of amorphous donepezil hydrochloride. Amorphous donepezil hydrochloride is prepared by dissolving donepezil hydrochloride in a mixture comprising an alcoholic solvent and a chlorinated solvent; and removing the solvents from the solution. The solvents can be removed by techniques such as vacuum drying, lyophilization, distillation under vacuum, freeze drying, spray drying, etc. The alcoholic solvent is selected from the group consisting of methanol, ethanol, isopropyl alcohol, tert-butyl alcohol and n-butyl alcohol. Methanol is a preferred solvent. The suitable chlorinated solvents are chloroform, methylene dichloride, carbontetrachloride and ethylene dichloride. Methylene dichloride and chloroform are preferred solvents.

BRIEF DESCRIPTION OF THE DRAWING

FIG. 1 is a x-ray powder diffraction spectrum of amorphous donepezil hydrochloride.

x-Ray powder diffraction spectrum was measured on a Siemens D5000 x-ray powder diffractometer having a copper-Kα radiation.

The following examples further illustrate the invention.

EXAMPLE 1

Donepezil hydrochloride (10 gm, obtained by the process described in example 4 of EP 296560) is dissolved in the mixture of methanol (50 ml) and chloroform (50 ml). The solution is subjected to vacuum drying at about 40° C. for 10 hours to give 9.1 gm of amorphous donepezil hydrochloride.

EXAMPLE 2

Example 1 is repeated by subjecting the solution to spray drying instead of vacuum drying using nitrogen gas to give amorphous donepezil hydrochloride.

EXAMPLE 3

Crystalline donepezil hydrochloride (10 gm) is dissolved in the mixture of ethanol (60 ml) and chloroform (50 ml). The solution is subjected to vacuum drying at about 45° C. for 9 hours to give 9.2 gm of amorphous donepezil hydrochloride.

EXAMPLE 4

Example 3 is repeated by subjecting the solution to spray drying using nitrogen gas instead of vacuum drying to give amorphous donepezil hydrochloride.

We claim:

1. A process for preparation of amorphous donepezil hydrochloride, which comprises:
   a) dissolving donepezil hydrochloride in a mixture of an alcohol and a chlorinated solvent; and
   b) removing the solvents from the solution;

wherein the alcohol is selected from the group consisting of methanol, ethanol, and isopropyl alcohol, and the chlorinated solvent is selected from the group consisting of chloroform, and methylene dichloride.

2. A process according to claim 1, wherein the solvents are removed by vacuum drying.

3. A process according to claim 1, wherein the solvents are removed by spray drying.

4. A process according to claim 1, wherein the alcohol is methanol or ethanol and the chlorinated solvent is methylene dichloride or chloroform.

5. A process for preparation of amorphous donepezil hydrochloride, which comprises:
   a) dissolving donepezil hydrochloride in a mixture of an alcohol and a chlorinated solvent; and
   b) removing the solvents from the solution;

wherein the alcohol is selected from the group consisting of methanol and ethanol, and the chlorinated solvent is chloroform.

6. A process according to claim 5, wherein the solvents are removed by vacuum drying.

7. A process according to claim 5, wherein the solvents are removed by spray drying.

* * * * *